(12) United States Patent
Brons et al.

(10) Patent No.: US 7,708,864 B2
(45) Date of Patent: May 4, 2010

(54) METHOD FOR REFINERY FOULANT DEPOSIT CHARACTERIZATION

(75) Inventors: Glen Brons, Phillipsburg, NJ (US); Leo D. Brown, Baton Rouge, LA (US); Himanshu Joshi, Chester, NJ (US); Raymond J. Kennedy, Hampton, NJ (US); Tom Bruno, Raritan, NJ (US); Thomas M. Rudy, Warrenton, VA (US)

(73) Assignee: ExxonMobil Research & Engineering Company, Annandale, NJ (US)

( * ) Notice: Subject to any disclaimer, the term of this patent is extended or adjusted under 35 U.S.C. 154(b) by 1221 days.

(21) Appl. No.: 11/173,979

(22) Filed: Jul. 1, 2005

(65) Prior Publication Data

US 2006/0014296 A1    Jan. 19, 2006

Related U.S. Application Data

(60) Provisional application No. 60/588,743, filed on Jul. 16, 2004.

(51) Int. Cl.
*C10B 43/14* (2006.01)
(52) U.S. Cl. .................. 201/1; 73/23.38; 374/14; 436/908; 436/173; 436/805
(58) Field of Classification Search .................. 436/173, 436/908, 805; 208/131, 188; 44/1 C; 201/1; 374/14; 73/23.38
See application file for complete search history.

(56) References Cited

U.S. PATENT DOCUMENTS 4,313,737 A * 2/1982 Massey et al. ................. 241/1
4,410,418 A * 10/1983 Kukes et al. ............... 208/48 R
4,477,337 A * 10/1984 Ronden et al. .............. 208/188
4,490,244 A * 12/1984 Stecker ....................... 208/131
5,997,723 A    12/1999 Wiche et al.

OTHER PUBLICATIONS

Gentzis et al., Microscopy of fouling deposits in bitumen furnaces, 2000, Elsevier Science Ltd., P1173-1184.*
Cai et al., Coke formation in steam crackers for ethylene production, 2002, Elsevier Science B.V., P199-214.*
Holmes et al., A solvent extraction method to study the location and concentration of coke formed on zeolite catalysts, 1997, Elsevier Science B.V., P355-372.*

* cited by examiner

*Primary Examiner*—Tony G Soohoo
*Assistant Examiner*—Robert Eom

(57) ABSTRACT

The present invention is a method to identify a refinery solid foulant of unknown composition including the following steps: obtaining a solid foulant sample, removing trapped feed from the sample with a solvent to obtain an insoluble sample, scanning the insoluble sample with a scanning electron microscope and energy dispersive x-rays, performing a thermal gravimetric analysis including an ash test on the insoluble sample to determine the presence of polymer, coke and inorganic elements, performing an elemental analysis on the insoluble sample for the elements carbon, hydrogen, sulfur, nitrogen, halogens, and metals, performing an optical microscopy on the insoluble sample to determine the presence of wax, asphaltenes, anisotropic coke and isotropic coke, and identifying the solid foulant.

9 Claims, 3 Drawing Sheets

Flow Diagram of the Analysis of Solid Foulant

Flow Diagram of the Analysis of Solid Foulant

FIGURE 2
Pictorial of Foulant Deposit 21060-136-12
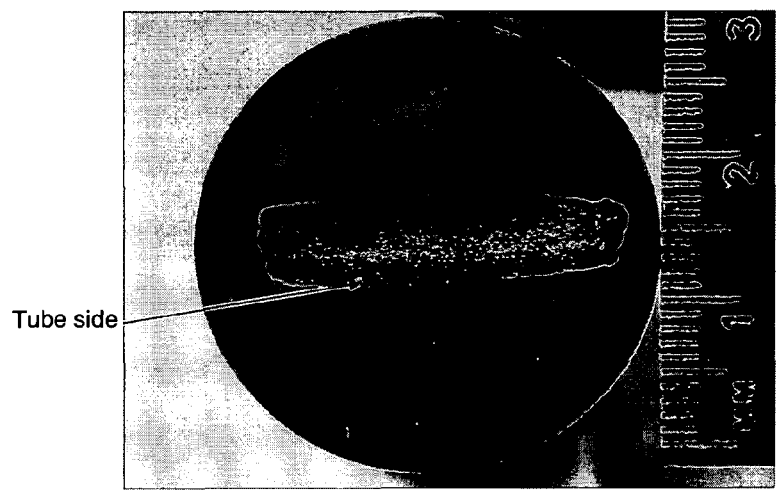
FIGURES 3a and 3b
SEM Scan and Element Map of Foulant Deposit 21060-136-12
Figure 3a
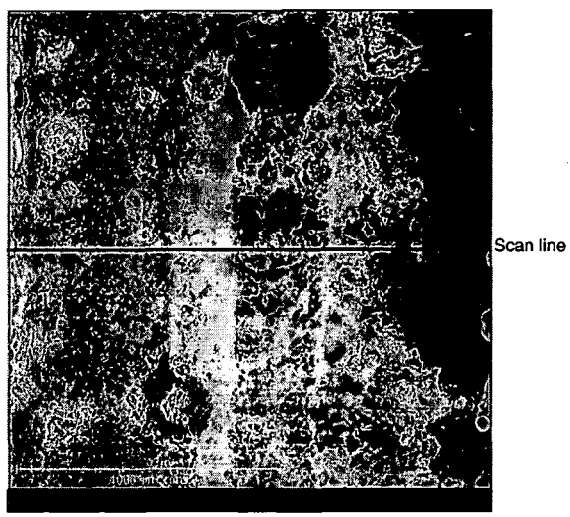
Figure 3b
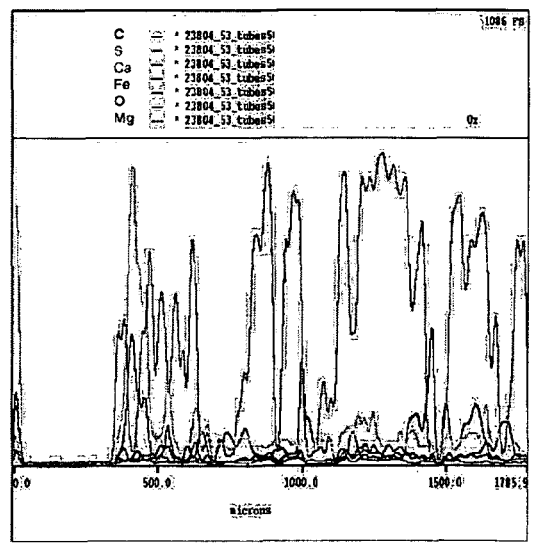

SEM/EDX Scan Determines Major Elements in Foulant 21060-136-12

METHOD FOR REFINERY FOULANT DEPOSIT CHARACTERIZATION

This application claims the benefit of U.S. Provisional Application No. 60/588,743 filed Jul. 16, 2004.

BACKGROUND OF THE INVENTION

The present invention is a method to identify the chemical composition of an unknown refinery solid foulant deposit. This invention provides a procedure, which enables refinery and support laboratory personnel to better coordinate the diagnosis and solution of the most common hydrocarbon fouling problems in refining by having an accurate understanding of what the foulant material is. Although the examples used in this report focus on refining, the protocol described is also fully applicable to chemical plant and upstream unit fouling analyses.

Petroleum refining includes a number of different method units. Fouling of a method unit is caused by the accumulation of an unexpected phase in a method unit. This phase is often a solid that accumulates on the surfaces of the method equipment that is designed to handle flowing liquids or gases.

Even low amounts of foulant increase energy costs by reducing the heat efficiencies. Moderate fouling decreases the efficiency of the method unit while high fouling reduces flow and increases pressure drop until the unit needs to be shut down for cleaning. More severe fouling can and has resulted in unplanned unit shut downs.

SUMMARY OF THE INVENTION

The present invention is a method to identify the chemical composition of an unknown refinery solid foulant deposit. Such an invention is needed for one to determine the cause of the fouling problems by hydrocarbon streams in petroleum refining. The invention is based upon compositional analysis of the foulant deposit recovered from the fouled unit and on knowledge of the most common causes of refinery fouling. A standard protocol for determining such compositions of unknown materials does not exist and is needed for mitigation of said fouling. Once the composition of the foulant deposit is determined, possible mitigation methods can be proposed. The refinery then can select the most cost-efficient mitigation strategy that best meets the need.

Because fouling is such a broad and dispersed subject with causes crossing many technological and method boundaries, it is essential that the analysis of a root cause be based on a consistent and repeatable work method. Only in this way, can what is learned from one plant or method unit be shared/compared to establish similar root causes and associated mitigation techniques. The lack of this common thread of data sharing has been an impediment to experience sharing in the past.

The method to identify the refinery solid foulant of unknown composition include the following steps: obtaining a solid foulant sample, removing trapped feed from the sample with a solvent to obtain an insoluble sample, scanning the insoluble sample with a scanning electron microscope and energy dispersive x-rays, performing a thermal gravimetric analysis, including an ash test on the insoluble sample to determine the relative amounts of polymer, coke and/or inorganic elements, performing an elemental analysis on the insoluble sample for the elements carbon, hydrogen, sulfur, nitrogen, halogens, and metals to quantify each element, performing optical microscopy on the insoluble sample to determine the presence of wax, asphaltenes, anisotropic coke and isotropic coke, and thereby identify the chemical composition of the solid foulant deposit.

BRIEF DESCRIPTION OF THE DRAWINGS

FIG. 2 shows a representative fouling deposit from a fouled refinery pre-heat train exchanger in Example 1.

FIG. 3(a) shows a scanning electron microscope (SEM) picture of the deposit in Example 1.

FIG. 3(b) shows an energy dispersive x-ray (EDX) scan along the scan line of FIG. 4.

DETAILED DESCRIPTION OF THE PREFERRED EMBODIMENTS

Figure 1:
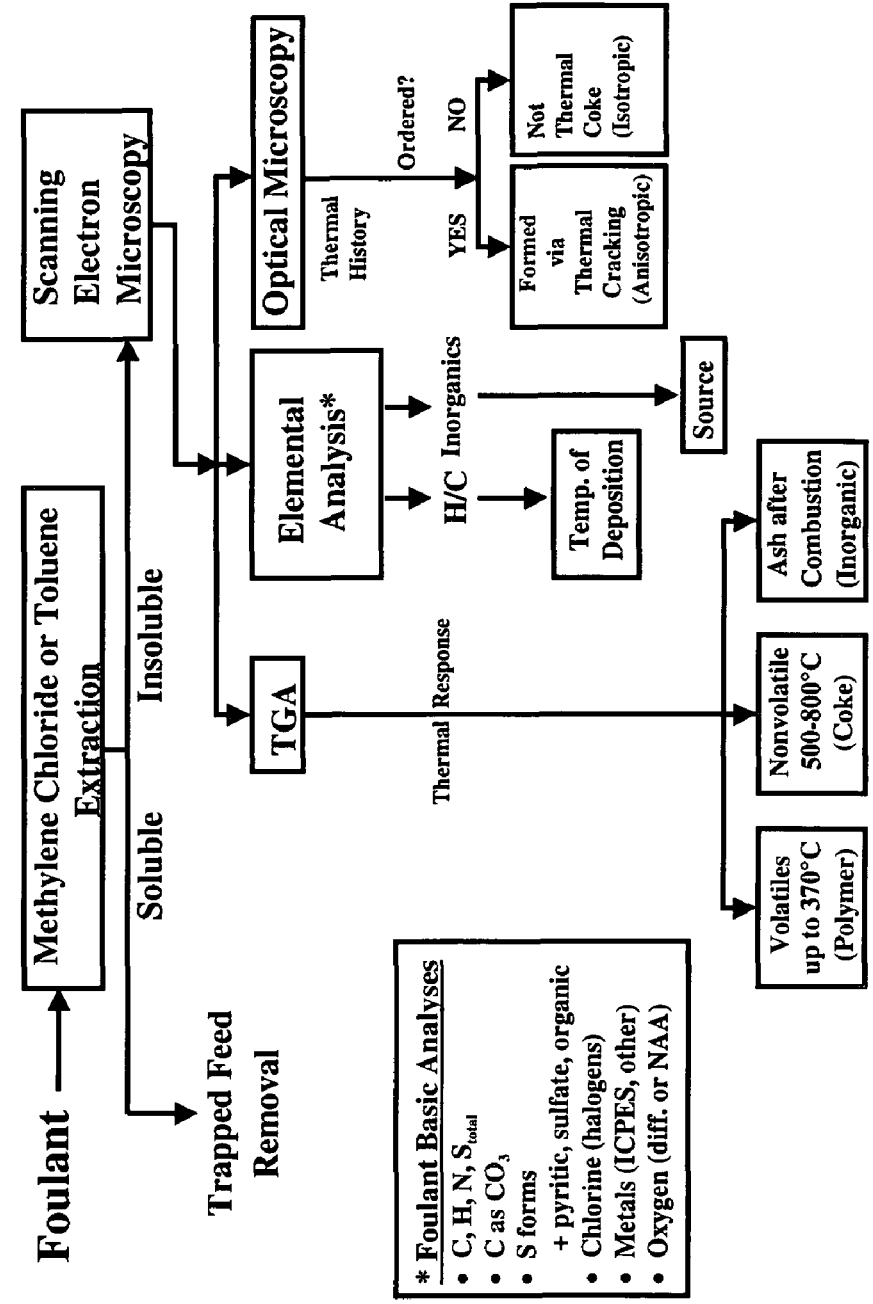
FIG. 1 is a flow diagram of the analysis of solid foulant.

The present invention is a method to identify the chemical composition of an unknown refinery fouling deposit.

The basis of the present invention is that most refinery fouling is the result of some more common causes that can be detected and verified by determining the chemical composition by standardized analytical testing. Fouling causes can be divided into five general classes with refinery examples under each class:

1. Scaling: precipitation of salts from water solution onto heat transfer surfaces.
    a. Sea salts from crude oil containing dispersed water
    b. Salt or scale deposition from treated/untreated cooling system water
2. Corrosion Fouling: the reaction of the heat transfer surface to form corrosion products.
    a. Iron sulfide formation by reactive sulfur or hydrogen sulfide
    b. Iron naphthenate formation by naphthenic acids in the oil and possible subsequent reactions with hydrogen sulfide to form iron sulfide
3. Precipitation Fouling: formation of an insoluble phase by cooling, by mixing two or more streams, or by breaking an emulsion within the fouled unit.
    a. By Cooling
        i. Wax deposition by cooling below the freezing temperature of high molecular weight paraffins
        ii. Asphaltene deposition by cooling converted resid, such as by Visbreaking™ or Residfining™
    b. By Blending
        i. Mixing incompatible oils in the wrong proportions that can result in the precipitation of asphaltenes or waxes.
    c. By Breaking an Emulsion
        i. Breaking a hydrocarbon in water emulsion, such as by heating
4. Chemical Reaction Fouling: formation of an insoluble phase by chemical reaction between components in the fluid.
    a. Thermal Coking (asphaltene insolubility during thermal cracking)
    b. Polymerization of conjugated olefins
    c. Aromatic Growth
    d. Oxidation
    e. Ammonium Chloride, Bisulfide, etc. formations
    f. Others
5. Particulate Fouling: dispersed particles formed upstream and carried over to and deposited within the fouled unit.
    a. Coke
    b. Asphaltenes
    c. Iron Sulfide d. Catalyst Fines e. Others Fouling often results from a combination of and/or a series of these causes. Hence, characteristics have been determined which can identify each of these common causes of fouling based on the chemical composition of the deposit. As a result, a sequence of analytical tests for the foulant recovered from the fouled unit were designed to diagnose the cause(s) of fouling.

It is extremely important that accurate records are made of the location and approximate quantity of foulant as well as method conditions during and before the fouling was noticed. Pictures of the foulant on the unit are also very helpful. Important method conditions needed for the root-cause determination include temperature, pressure, flow rate (residence time), source of the method fluids, details on the geometry of the unit, and metallurgy of the method unit. Is this a first occurrence of fouling for the unit? When did fouling begin? When and what were the method upsets of the unit? These kinds of questions about the method unit should be answered as part of the method history. If the method history suggests possible fouling causes, they should be noted.

For example, if a foulant is obtained from a heat exchanger, it is important to know if the sample came from within the tubes, on the tubesheet face, or on an unheated surface of the channel box. This knowledge, which implies surface temperatures, metallurgy, and velocity factors, can provide valuable clues to the foulant source compared to just stating that the foulant was retrieved from a particular exchanger.

Care should be taken to ensure that the foulant sample is representative and not contaminated by collection or flushing procedures. If it is also clear that there are different types of foulants, they should each be sampled. Ideally, about 100 grams of foulant should be collected for each sample. If this is not possible, as much sample as possible should be collected (much can be learned from even one gram of sample). The sample should be stored in a closed container until analysis is made.

Analysis of Solid Foulant Samples

A flow diagram in FIG. 1 shows the procedure for analyzing solid foulant samples. Descriptions of each of the analytical tests are given in Appendix I. The first step is to allow 10 to 25 grams of the sample to soak for at least four hours in toluene, or other solvent with similar solvent capability, to dissolve trapped feed from the foulant. After filtration, the remaining solids are washed with additional solvent until a clear filtrate is obtained. The insoluble solids are then dried in a vacuum oven at 70° C. (158° F.) for at least 1-2 hours. If the entire foulant dissolves in the solvent, the procedure should be repeated on another sample of the foulant replacing toluene with n-heptane to obtain insoluble asphaltenes. This washing procedure is important so that subsequent results can be ascribed to the foulant rather than a mixture of foulant and trapped feed.

It is important that a homogeneous sample be obtained prior to the TGA and elemental/metals analyses. This can be achieved by grinding the foulant sample to −60 mesh and mixing thoroughly before the analytical tests are carried out. Often this is best done after the toluene extraction. However, if the foulant is a hard, granulated solid (not paste-like), this may be done before toluene washing.

Before the above grinding and homogenizing of the entire sample, a toluene insolubles, unground portion of the foulant is subjected to scanning electron microscopy (SEM) and energy dispersive x-ray (EDX) to first qualitatively identify the elements present and their association with each other. SEM is an essential step for this method. This information is used to identify which elements are needed for subsequent quantification on the toluene insoluble, ground and homogenized sample to determine the amount(s) of different materials that may be present in the foulant deposit—as per the steps of FIG. 1.

The first part of the analysis step is to determine how much of the insoluble foulant is due to inorganics (metals, salts, corrosion products, etc.) and how much is due to organics (high molecular weight waxes, coke, etc.).

Inorganic Fouling

The initial step after the SEM and EDX is to determine how much of the insoluble sample is due to inorganics. This can be achieved with an elemental analysis for carbon, hydrogen, sulfur, nitrogen, chlorine (halogens) and metals contents and ash test, which is part of the thermal gravimetric analysis (TGA). Analysis for oxygen and other elements may also be done if the other elements add up to significantly less than 100% (90% or lower) or if there is reason to suspect that they are present.

If the sample contains 10-15 wt. % or greater inorganics and it is confirmed that it was not part of the metal surface of the unit removed with the foulant, inorganic fouling should be addressed first. Although there can be more than one cause, the deposition of inorganics can also promote the deposition of organics by allowing for increased surface areas for asphaltenes, for example, to lay down and thermally degrade to coke. Elemental analysis will suggest if the primary cause is due to iron sulfide (common), sea salts, ammonium chloride, aluminum silicate or others.

Organic Fouling

If the toluene-insoluble portion of the foulant sample is less than 10-15 wt. % inorganic, the bulk of the foulant may be due to coke or high molecular weight waxes. The cause of the organic fouling should be determined.

The composition of the inorganics may be used to trace the origin of the organic fouling precursors. For example, vanadium and nickel are naturally connected to organics as porphyrins and are soluble in crude oils and resids. Thus, these metals can indicate entrained resid in a gas oil stream for example. Nevertheless, the next step is to determine by optical microscopy, using cross-polarized light, whether the foulant is isotropic (unordered) or anisotropic (ordered) coke. One determines whether or not the coke is ordered or unordered by the patterns observed with the microscope. For example, the anisotropic (ordered) coke exists as distinct patterns of varying shapes or types, while the isotropic (unordered) has no distinguishable formation patterns.

Anisotropic coke derived from carbonaceous mesophase shows that it was formed by thermal cracking followed by phase separation of insoluble asphaltenes, such as the coking of resid. If the coke is isotropic, a possible cause is the initial polymerization of conjugated olefins. The presence of significant volatiles below 370° C. (700° F.) in thermal gravimetric analysis (TGA) may be an indication that the cause is polymerization. The other indication is that polymerization usually occurs in condensed liquid products of thermal cracking (such as from cokers) after being held at 232-324° C. (450-615° F.). Asphaltenes can also become insoluble by blending oils containing asphaltenes with oils high in saturates or cooling a thermally converted oil, such as a Visbreaker™ tar. TGA volatiles between 500-800° C. (932-1,472° F.) are typically observed when coke exists in the deposit. During combustion with oxygen at 800° C. (1,472° F.), additional coke is 'volatilized' from the sample, leaving only ash which is due to metals in the deposit that now exist in an oxide state.

Finally, the hydrogen to carbon atomic ratio (H/C=wt. % hydrogen multiplied by 11.92 and divided by wt. % carbon) of the coke can be roughly correlated with the temperature of deposition This can help to determine if the coke was formed at a higher temperature upstream of the fouled unit, if the temperature was higher than measured, if the coke had been present for significant lengths of time, or if a catalytic mechanism was involved. It is known from the literature that asphaltenes have atomic ratios in the 1.0-1.2 range, coke materials have lower H/C ratios while waxes can be as high as 2.0. It is also important to correlate H/C ratios with findings from microscopy. The H/C ratio is an average value of the homogenized sample, which may contain different types of coke.

If the foulant is soluble in toluene, but insoluble in n-heptane, it is an asphaltene by definition. Thus, it is formed by one of the two mechanisms discussed above but was not heated enough to degrade to coke (coke is defined as toluene insoluble). While it is usually clear from the method conditions which mechanism applies, a general indication that the asphaltenes were thermally cracked is that they have an atomic H/C ratio less than one.

Key characteristics used to identify common causes of fouling in refinery foulant sample, and guidance on how to trace them are summarized in Table 1.

TABLE 1

Key Characteristics to Identify and Trace Common Causes of Fouling

| | Fouling Cause | Foulant Evidence |
|---|---|---|
| 1. | Sea salts: NaCl, MgCl$_2$, CaCl$_2$ | Toluene-insol.; ash >10-15%; metals: Na, Ca, Mg; high Cl |
| 2. | Iron sulfide | Toluene-insol.; ash >10-15%; most metals: iron; high sulfur |
| 3. | Wax deposition | H/C >1.7, melting point transition Microscopy: clear but bright white in cross-polarized light |
| 4. | Asphaltene deposition by cooling | Toluene-sol./n-heptane-insol. |
| 5. | Asphaltene deposition by blending | Toluene-insol. isotropic or Toluene-sol./n-heptane insol. |
| 6. | Hydrocarbon in water emulsion | Deposition on heating close to 93° C. (200° F.) |
| 7. | Thermal coking | Toluene-insol.: anisotropic, H/C <0.6 |
| 8. | Polymerization of conjugated olefins | Toluene-insol.: isotropic coke, formed between 232-324° C. (450-615° F.) |
| 9. | Aromatic growth | Toluene-insol.: isotropic coke |
| 10a. | Ammonium chloride | Water soluble; high in N and Cl |
| 10b. | Ammonium bisulfide | Water soluble; high in N and H$_2$S |

Example 1

Figure 4:
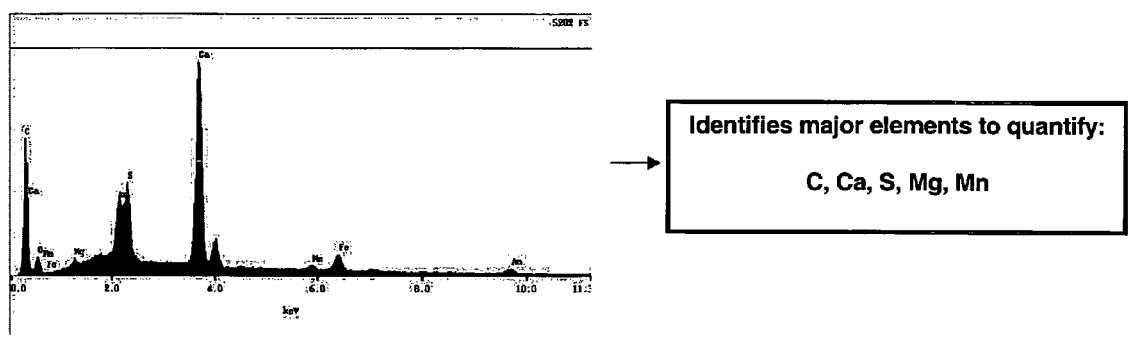
FIG. 4 shows the identity of the major elements from SEM/EDX scan of Example 1.

The method of the present invention was applied to a fouling deposit from a fouled refinery pre-heat train exchanger. FIG. 2 shows a pictorial of the fouling deposit. FIGS. 3a and 3b show an SEM scan and the element map of the deposit. FIG. 4 shows the major elements to quantify from the SEM/EDX scan. Table 2 gives the analytical results on this fouling deposit. The resulting overall composition of this deposit was found to be predominately calcium carbonate and iron sulfide with lesser amounts of other salts.

TABLE 2

Analytical Results on Foulant Deposit Example 1

| Location Extraction Data | Tubeside | |
|---|---|---|
| | Toluene Insol. | Oil |
| Wt. % | 100 | 0 |

SOLIDS ANALYSIS

| Elements | Wt. % | |
|---|---|---|
| Carbon | 10.38 | |
| Hydrogen | <0.5 | |
| Nitrogen | <0.5 | |
| Total S | 7.96 | |
| | 6.25 | Pyritic S |
| | 1.37 | Organic S |
| | 0.34 | Sulfate S |
| C as CO3 | 9.43 | |
| Fe | 6.33 | |
| Al | 0.10 | |
| Ca | 25.30 | |
| Mg | 1.76 | |
| Mn | 1.21 | |
| Zn | 0.52 | |
| O as CO3 | 37.72 | |

| TGA Data | Wt. % |
|---|---|
| Relative volatiles <370° C. | 0.0 |
| Total wt. loss to 500° C. | 1.0 |
| Total wt. loss to 800° C. | 27.0 |
| Combustion loss (at 800° C.) | 0.0 |
| Ash | 73.0 |

APPENDIX I

Analytical Tests

The analytical tests used for the analyses of solid foulants are listed below with known, established procedure method information. These tests are more typically carried out on the toluene-insoluble fractions of solid foulants, which have also been ground to below 60 mesh and homogenized. Added notes on some of these tests are provided below.

| Analysis | Procedure |
|---|---|
| Carbon and Hydrogen (combustion, ≧0.5%) | ASTM D5373/D5291 |
| Carbon, Hydrogen, Nitrogen (combustion, ≧0.5%) | ASTM D5373/D5291 |
| Nitrogen (Kjeldahl)[a] | ASTM D3179 Mod./E778 Mod. |
| Sulfur, Total (>0.05%) | ASTM 4239, Method C |
| Sulfur, Total (<0.05%) | ICP-OES/ASTM D129/D4327 |
| Total Halogens Reported as Chlorine | ASTM E442/D2361 |
| Thermogravimetric Analysis (TGA)[b] | See note b below. |
| Metals[c] | ICP-OES, FLAA, CVAA, or GFAA |
| Sulfur Forms (total, pyritic, sulfate, organic) | ASTM D2492 Mod. |
| Carbon as Carbonate | ASTM D513(B) Mod. for Solids |
| NMR - Aromatic C/Aliphatic C ratio[d] | See note d below. |
| Melting Point (for waxes)[e] | See note e below. |
| X-Ray Diffraction (XRD)[f] | See note f below. |
| Optical Microscopy[g] | See note g below. | a) It is recommended that for nitrogen contents below 0.5 wt. %, the more accurate measurement should be made using the Kjeldahl technique.

b) TGA heats a representative sample from 30 to 800° C. under an inert atmosphere (nitrogen or argon) while measuring wt. % losses as a function of temperature. Oxygen is then introduced at 800° C. for complete combustion and ash content (inorganics) measurements.
c) Inductively Coupled Plasma Optical Emission Spectroscopy (ICP-OES), Flame Atomic Absorption (FLAA), Cold Vapor Atomic Absorption (CVAA), or Graphite Furnace Atomic Absorption (GFAA).
d) Nuclear Magnetic Resonance ($^{13}C$) can be used if one needs to determine the ratio of aromatic to aliphatic carbon.
e) Melting points should be measured when high atomic H/C foulants (waxes) have been identified.
f) Identifies specific crystalline phases of inorganic components such as the type of iron sulfide present in corrosion scale. XRD can also be used to find the degree of graphitization in anisotropic coke.
g) Optical microscope samples are prepared by embedding the washed solid foulant in epoxy, followed by a series of standard grinding and polishing procedures. The highly polished cross-section of each foulant sample is then examined under cross-polarized light. Observations to be made on the sample include general morphology, particle size, degree of anisotropy, reflectance, porosity and inclusions (e.g., metal sulfides).

Calculations

Wt. % Oxygen/Unknowns (diff.): 100−(% C+% H+% N+% S+% Cl+% Metals)

Atomic H/C Ratio:

$$\frac{\text{Wt. \% Hydrogen}}{\text{Wt. \% Carbon}} \times \frac{12.011 \text{ (atomic wt. C)}}{1.008 \text{ (atomic wt. H)}} = \text{atomic H/C ratio}$$

Transmission Optical Microscopy

This test requires a laboratory microscope that can magnify to 250× and preferably to 400×. For several uses the ability to observe in transmitted cross-polarized light is required. To identify anisotropic coke in cross-polarized light, an intense light source, such as a halogen or a xenon lamp, may be required. Although most uses provide only qualitative information, transmission microscopy impart can impart much insight as to the causes of fouling.

The most useful application is observing a representative drop of the oil or other liquid entering and leaving a fouled method unit. The drop is placed on a clean microscope slide and covered by a cover slip slide. First at 100× focus the microscope on the resulting liquid film and determine if there are any insoluble particles or liquids. One should look for many particles or insoluble liquids over the entire view and not a few isolated specs. If none are seen under normal light, the next step is to examine the sample under cross-polarized light. Wax particles are clear in normal light but show up as bright white in cross-polarized light. Most wax does not cause fouling because it dissolves on heating near its melting point. However, if the solid foulant is identified as containing a large fraction of wax, observing wax in the feed or product of a fouled unit is significant. If a large number of particles or insoluble liquids are observed, focus on one and use the maximum magnification to identify with the following characteristics:

| Fouling Cause | Characteristics Under Microscope |
|---|---|
| 1. Wax | Clear in normal light. Bright plates or needles under cross-polarized light. |
| 2. Asphaltenes | Agglomerates of small particles to form brownish, curved chains in normal light and dark under cross-polarized light. |
| 3. Anisotropic Coke | Black particles in normal light but orange with black brushes in cross-polarized light that move when the microscope stage is rotated. |
| 4. Isotopic Coke | Black particles in both normal light and cross-polarized light. |
| 5. Iron Sulfide | Black particles in both normal light and cross-polarized light. |
| 6. Salt | Clear cubic shaped crystals in normal light. |
| 7. Water Drops | Spherical, clear regions that turn color when sample is blended with a water-soluble dye. |

Reflected optical microscopy of polished surfaces of solid foulants is the best method to identify foulants. However, this requires more expertise than using transmitted light. Thus, an alternative is to break up the foulant and disperse it in a liquid of low volatility, such as hexadecane, 1-methyl naphthalene, o-dichlorobenzene or quinoline. The same characteristics as above can be used to identify the foulant as well as for the solubility behavior in these liquids. For example, asphaltenes are insoluble in hexadecane but soluble in the other three liquids.

What is claimed is:

1. An analytical protocol to identify a refinery solid foulant of unknown composition caused by scaling, corrosion, precipitation, chemical reaction, or particulate fouling comprising
   a) obtaining a homogeneous foulant sample which is subjected to a series of tests and evaluations to identify the foulant,
   b) removing rapped feed from said sample with a solvent to remove any soluble sample and to obtain an insoluble sample,
   c) scanning said insoluble sample with scanning electron microscopy,
   X-ray Diffraction and energy dispersive x-rays to qualitatively identify the elements present,
   d) grinding and mixing said insoluble sample to obtain a homogeneous insoluble sample;
   e) performing a thermal gravimetric analysis including an ash test on the homogeneous insoluble sample to determine the presence of organic polymer, coke and inorganic elements, and if said homogenous insoluble sample contains about 10-15% or greater inorganics, go to step f), and if not, go to step g),
   f) performing an elemental analysis on the homogeneous insoluble sample to determine the elements carbon, hydrogen, sulfur, nitrogen, halogens, and metals, and hydrocarbon to carbon ratio to correlate with temperature of deposition,
   g) performing an optical microscopy on the homogeneous insoluble sample to determine the presence of wax, asphaltenes, anisotropic coke and isotropic coke, and
   h) relating the composition, amounts and characteristics of both the inorganics and organic determined in the steps above to determine the cause and identity of the composition of the solid refinery foulant.

2. The method of claim 1 wherein said step of removing trapped feed from said sample is performed with the solvent toluene, xylenes, methylene chloride or combinations thereof.

3. The method of claim 1 wherein said thermal gravimetric analysis is performed by determining volatiles up to about 370° C., non-volatiles between 500-800° C., and ash after burn.

4. The method of claim 1 wherein said elemental analysis includes determining the atomic H to C ratio for said elements.

5. The method of claim 1 wherein said stop of optical microscopy is performed using cross-polarized light.

6. The method of claim 1 further comprising the step of performing a nuclear magnetic resonance on said sample.

7. The method of claim 1 further comprising the step of measuring the melting points of said sample.

8. The method of claim 1 wherein said step of performing said optical microscopy is carried out by embedding said sample in epoxy.

9. The method of claim 1 wherein said of performing said optical microscopy is carried out to determine if coke that is present is ordered or unordered.

* * * * *